US012042224B2

(12) United States Patent
Leube et al.

(10) Patent No.: US 12,042,224 B2
(45) Date of Patent: Jul. 23, 2024

(54) METHOD AND DEVICE FOR DETERMINING AT LEAST ONE ASTIGMATIC EFFECT OF AT LEAST ONE EYE

(71) Applicant: Carl Zeiss Vision International GmbH, Aalen (DE)

(72) Inventors: Alexander Leube, Aalen (DE); Arne Ohlendorf, Tübingen (DE); Eric Nehrbass, Aalen (DE); Siegfried Wahl, Donzdorf (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 18/165,448

(22) Filed: Feb. 7, 2023

(65) Prior Publication Data

US 2023/0181029 A1    Jun. 15, 2023

Related U.S. Application Data

(63) Continuation of application No. PCT/EP2021/084535, filed on Dec. 7, 2021.

(30) Foreign Application Priority Data

Dec. 8, 2020 (EP) ..................................... 20212484

(51) Int. Cl.
*A61B 3/036* (2006.01)
*A61B 3/00* (2006.01)

(52) U.S. Cl.
CPC ............ *A61B 3/036* (2013.01); *A61B 3/0033* (2013.01); *A61B 3/0041* (2013.01)

(58) Field of Classification Search
CPC .................................................... A61B 3/036
(Continued)

(56) References Cited

U.S. PATENT DOCUMENTS 1,467,500 A * 9/1923 Reaves .................. A61B 3/036
351/244
1,564,495 A * 12/1925 Sheard .................. A61B 3/036
351/243

(Continued)

FOREIGN PATENT DOCUMENTS

DE         4131799 A1    3/1993
EP         2842479 A1    3/2015
(Continued)

OTHER PUBLICATIONS

Raubitschek; "Die Bestimmung des Astigmatismus mittels der Pfeilschattenprobe," Zeitschrift für Augenheilkunde. 72(6), 337 to 353, 1930; with human translation (Year: 1930).*

(Continued)

*Primary Examiner* — Zachary W Wilkes
(74) *Attorney, Agent, or Firm* — Tautz & Schuhmacher LLC; Georg Hasselmann

(57) ABSTRACT

A method, a computer program, and a device for determining at least one astigmatic effect of at least one eye of a person are disclosed, as well as a related method for producing at least one spectacle lens for the at least one eye of the person. The method for determining the astigmatic effect includes:
a) displaying an image to an eye of the person, the image including a line with a plurality of sections, wherein an orientation of each section with respect to an optical axis of the image differs from each other, respectively;
b) recording a reaction of the person to the image at at least one point in time; and
c) determining at least one value for at least one astigmatic effect of at least one eye of the person by evaluating the at least one reaction of the person at the point in time.

14 Claims, 3 Drawing Sheets

(58) Field of Classification Search
USPC .................................................. 351/239, 241
See application file for complete search history.

(56) References Cited

U.S. PATENT DOCUMENTS

| | | | | |
|---|---|---|---|---|
| 4,660,948 | A * | 4/1987 | Retz | A61B 3/02 351/203 |
| 7,367,675 | B2 * | 5/2008 | Maddalena | A61B 3/028 351/239 |
| 9,492,074 | B1 * | 11/2016 | Lee | A61B 3/036 |
| 2004/0135970 | A1 | 7/2004 | Koest | |
| 2007/0195264 | A1 | 8/2007 | Lai | |
| 2015/0150445 | A1 | 6/2015 | Iravani et al. | |
| 2021/0275012 | A1 * | 9/2021 | Prevoo | A61B 3/036 |

FOREIGN PATENT DOCUMENTS

| | | |
|---|---|---|
| WO | 0200105 A1 | 1/2002 |
| WO | 2011133945 A1 | 10/2011 |

OTHER PUBLICATIONS

Bannon Re. Recent developments in techniques for measuring astigmatism. Am J Optom Arch Am Acad Optom. Jul. 1958;35(7):352-359. doi: 10.1097/00006324-195807000-00003. PMID: 13559367 (Year: 1958).*

Raubitschek, "Die Bestimmung des Astigmatismus mittels der Pfeilschattenprobe," Zeitschrift für Augenheilkunde. 72(6), 337 to 353, 1930, and English-language machine translation thereof.

Raubitschek, "The Raubitschek arrow test for astigmatism," American Journal of Ophthalmology. 35(9), 1334 to 1339, 1952.

Thibos et al., "Power Vectors: An Application of Fourier Analysis to the Description and Statistical Analysis of Refractive Error", Optometry and Vision Science, vol. 74, No. 6, pp. 367 to 375, 1997.

Murphy et al., "An assessment of the orthogonal astigmatism test for the subjective measurement of Astigmatism," Ophthalmic and Physiological Optics, 22(3), 194 to 200, 2002.

Industrial Norm "Ophthalmic optics—Spectacle lenses—Vocabulary (ISO 13666:2019)", English version EN ISO ISO 13666:2019, Dec. 2019.

European Search Report issued in EP 20 212 484.8 to which this application claims priority, mailed May 21, 2021.

International Search Report and Written Opinion issued in PCT/EP2021/084535 to which this application claims priority, mailed Mar. 14, 2022.

International Preliminary Report on Patentability issued in PCT/EP2021/084535 to which this application claims priority, mailed Nov. 4, 2022.

* cited by examiner

METHOD AND DEVICE FOR DETERMINING AT LEAST ONE ASTIGMATIC EFFECT OF AT LEAST ONE EYE

CROSS REFERENCE TO RELATED APPLICATIONS

This application is a continuation application of international patent application PCT/EP2021/084535, filed on Dec. 7, 2021 and designating the U.S., which claims priority to European patent application EP 20 212 484.8, filed on Dec. 8, 2020, both of which are hereby incorporated by reference in their entireties.

TECHNICAL FIELD

The present disclosure refers to a method, a computer program, and a device for determining at least one astigmatic effect of at least one eye of a person and to a related method for producing at least one spectacle lens for at least one eye of a person.

BACKGROUND

Various methods and devices for determining at least one refractive error of at least one eye of a person are known. Herein, the terms "refraction" or "refractive" refer to a bending of incident light entering the interior of the eye via the pupil. With respect to the present disclosure, determining at least one value for the at least one refractive error of the at least one eye of the person, particularly, comprises determining at least one value for at least one astigmatic effect of the at least one eye of the person. As generally used, the term "astigmatic effect" corresponds to a condition in which an optical system comprising one eye of the person forms at least two individual line images of a point object, typically, as a result of a toricity of at least one refracting surface of the eye of the person. As a result thereof, the astigmatic effect causes that light which impinges on the at least one eye is distributed on the retina in an unsymmetrical fashion, which may, in particular, results in a distorted and/or blurred vision of the person. In particular, the astigmatic effect of the eye of the person comprises both a spatial orientation of the astigmatic effect, also denoted by as "axis," and an extent of the astigmatic effect, also denoted as "power." To completely correct the astigmatic effect of the eye of the person, quantifying an extent of both the axis and the power of the astigmatic effect of the eye of the person is particularly typical.

For determining at least one astigmatic effect of the at least one eye of a person a subjective approach is, typically, applied in which an optometrist or an ophthalmologist performs an interactive test with the person. Alternatively or in addition, an objective approach can be used applied, in which the optometrist or the ophthalmologist uses an autorefractive device. Both methods address determining a spherical and a cylindrical refractive error of the at least one eye of a person.

However, the known approaches require a set of different lenses and knowledge of how to apply the lenses together with the patterns in order to determine at least one astigmatic effect of the at least one eye of a person. Herein, the known methods which function without using such devices apart from boards, such as a Snellen dials, are only capable of determining a presence but not an extent of the at least one astigmatic effect. As further indicated above, the sophisticated device which is, typically, used for the objective approach requires high investment, maintenance and operation expenses that cannot be afforded at every place, in particularly viewed on a global scale. Independently of the kind of approach, the presence of an optometrist or an ophthalmologist and a satisfactory communication between the optometrist or the ophthalmologist, on one hand, and the person, on the other hand, respectively, is, required, which is, however, not always possible.

DE 4 131 799 A1 discloses that the person being tested selects one of the decision possibilities by means of a control element. Glasses, filters and/or similar, which are interposed in the observation beam path of the person being tested are selected by the computer. The selection is on the basis of stored data and the decision made. Adjustments can also be carried out. These previous steps are repeated until the complete test program is fulfilled, i.e., for carrying out tests on the basis of prerequirements, stored data and the results of tests previously carried out by the computer. The computer stores all the determined values and a complete test and result record is produced. The method relieves strain on person being tested, optimizes communication between person and optician, and ensures workability for each person and delivers optimum results.

US 2004/0135970 A1 discloses an ophthalmic refractometer for objective determination of the refractive power of an eye comprising an optometer system for imaging a test mark on the retina of the eye and comprising an observation system for observation of the test mark imaged on the retina, whereby the optometer system and the observation system can be adjusted in mutual synchronization in relation to a reference setting, and a refractive power parameter of the eye can be determined from the difference between the setting at which the test is imaged on the retina at least partially with sharp contours and the reference setting. A digital recording device and a digital image processing unit are provided on the observation system, whereby digital image data of the test mark imaged on the retina can be recorded using the recording device and the resulting image data can be analyzed in the image processing unit by digital image processing to determine the refractive power parameter.

US 2015/0150445 A1 discloses vision monitoring and screening testing tools and help-seeking enablers that may be used individually as or in combination with vision monitoring and screening testing systems that improves patients' ability to recognize onset and progression of visual changes over time. Patients' ability to identify acute or chronic visual conditions on their own may drive earlier help-seeking behavior by the patient, enable earlier clinical diagnosis by an eye care specialist, and therefore resulting in earlier treatment and reduced likelihood of severe vision loss.

Murphy, P. J., Beck, A. J., & Coll, E. P. (2002), *An assessment of the orthogonal astigmatism test for the subjective measurement of Astigmatism*, Ophthalmic and Physiological Optics, 22(3), 194-200, describe an orthogonal astigmatism test (OAT) developed for assessing ocular astigmatism. This study compares the OAT with the Jackson crossed-cylinder (JCC), Raubitschek arrow (RA) and the fan and block (FB) (fan chart). Fifty emmetropes or corrected spherical ametropes (<0.25 DC of astigmatism) were recruited, with a visual acuity of at least 6/5 in both eyes. Pseudo-astigmatism was induced by placing a +0.75 DC lens in front of the right eye at a random axis. With the left eye occluded, each subjective test was performed in a random order and the correcting lens power and axis noted.

Raubitschek, E. (1930), *Die Bestimmung des Astigmatismus mittels der Pfeilschattenprobe*, Zeitschrift für Augenheilkunde. 72(6), 337-353 and Raubitschek, E. (1952), The Raubitschek arrow test for astigmatism, American Journal of Ophthalmology. 35(9), 1334-1339, describe a test for astigmatism. As summarized by Murphy (2002), see above, this method consists of a board with two paraboloid lines positioned on a rotating disc to produce an approximate arrowhead shape. Near the apex of the arrow the two lines approach and become parallel to each other, but without touching. As the lines curve away from this point they become increasingly separate to eventually point in opposite directions. As the paraboloid lines start parallel but end up in opposite directions at the base, all possible astigmatic meridians are represented. When the disc is rotated, the person having an astigmatism observes a dark shadow moving along one line of the arrow, corresponding to the meridian of greatest ocular refractive power. As the arrow is rotated further, the shadow moves along one line until it jumps from one line to the other. The correct axis is obtained when both lines appear equal, symmetrical and without shadows. The person then looks at a Bannon cross bisecting the arrow, where one of the dashed lines now appear clearer than the other. Negative powered cylindrical lenses are inserted, with their axis at 90° to the clearer line, until both dashed lines appear equally blurred. Finally, the spherical correction is modified to move the focus back on to the retina to produce the final correction.

Further, US 2007/195264 A1, EP 2 842 479, WO 2011/133945 A1, and WO 02/00105 describe the technological background of the disclosure as discussed herein.

SUMMARY

It is an objective of the present disclosure to provide a method, a computer program, and a device for determining at least one astigmatic effect of at least one eye of a person and a related method for producing at least one spectacle lens for the at least one eye of the person, which at least partially overcome the above-mentioned problems of the state of the art.

It is a particular objective of the present disclosure to be able to determine at least one value for the astigmatic effect of at least one eye of a person, specifically with regard to a power and an axis thereof, by applying a simple and easy-to-use approach. Thereby, it is desirable to determine the astigmatic effect without requiring an optometrist, an ophthalmologist, a set of measuring glasses and/or a sophisticated device, such as an autorefractive device, designated for this purpose. In particular, it is desirable to determine the astigmatic effect in a fashion which can be applied on a global scale to all kinds of persons, whereby difficulties with communication or compliance can be avoided as far as possible.

This problem is solved by a method, a computer program, and a device for determining at least one astigmatic effect of at least one eye of a person and a related method for producing at least one spectacle lens for the at least one eye of the person wherein at least one reaction of the person to a transition of an appearance of an object in at least one image is recorded. Exemplary embodiments, which might be realized in an isolated fashion or in any arbitrary combination, are discussed in detail below.

In a first aspect, the present disclosure relates to a method for determining at least one astigmatic effect of at least one eye of a person. The method comprises the following steps a) to c) which may, typically, be performed in the indicated order starting with step a) and continuing with step b) and, subsequently, with step c); however, a different order may be possible at least in part. Further, additional method steps might be provided which may be indicated herein or not. Further, two or all of the method steps might be performed simultaneously, at least partially. Further, at least one of the method steps might be performed twice or more than twice, in a repeated fashion.

The method for determining at least one astigmatic effect of at least one eye of a person comprises the following steps:
  a) displaying at least one image to at least one eye of a person, wherein the at least one image comprises at least one line, wherein the at least one line comprises a plurality of sections, wherein an orientation of each section with respect to an optical axis of the image differs from each other;
  b) recording at least one reaction of the person to the at least one image at at least one point in time; and
  c) determining at least one value for at least one astigmatic effect of at least one eye of the person by evaluating the at least one reaction of the person at the point in time, wherein the at least one reaction of the person to the at least one image comprises indicating a position on the at least one line, wherein the position on the at least one line refers to at least one transition from a first appearance of the portion at least one line to the person to a second appearance of the at least one line to the person, or vice versa, wherein the at least one value for the at least one astigmatic effect is determined from the position of the at least one transition on the at least one line.

According to the present disclosure, determining at least one refractive error of at least one eye of a person comprises determining at least one astigmatic effect of the at least one eye of the person. Instead of the term "person," a different term, such as "subject," "test person," "user," or "wearer of eye glasses," may also be applicable. Herein, the method can be used for individually determining the astigmatic effect of each eye of a person in a consecutive or in a simultaneous fashion. As generally used, the terms "refraction" or "refractive" refer to a bending of incident light entering an interior of the eye of a person via the pupil. As further generally used, the term "astigmatic effect" corresponds to a condition in which an optical system comprising one eye of the person forms two individual line images of a point object, typically, as a result of a toricity of at least one refracting surface of the eye of the person. As a result thereof, the astigmatic effect causes that light which impinges on the at least one eye is distributed on the retina in an unequal fashion, which may, in particular, result in a distorted and/or blurred vision of the person. In particular, the astigmatic effect of the eye of the person comprises both a spatial orientation of the astigmatic effect, also denoted by as "axis," and an extent of the astigmatic effect, also denoted as "power." For completely correct the astigmatic effect of the eye of the person, quantifying an extent of both the axis and the power of the astigmatic effect of the eye of the person is particularly typical.

The present method for determining at least one astigmatic effect of at least one eye of a person can, typically, be used in a method for producing at least one spectacle lens for the at least one eye of the person as described below in more detail. Based on standard ISO 13666:2019, also referred to herein as the "standard," Section 3.5.2, the term "spectacle lens" relates to an optical lens which is used within the framework of the present disclosure for determining and/or correcting a defective vision of a person, wherein the optical lens is carried in front of the eye of the person, thereby avoiding a direct contact with the eye.

In particular, the determining of the at least one refractive error of at least one eye of a person can comprise determining a spherocylindrical lens which is, in general, used as a spectacle lens to correct the at least one refractive error of the at least one eye of the person. For describing the spherocylindrical lens, various approaches are possible. As defined in the standard, Section 3.6.6, the term "spherocylindrical lens" refers to a spectacle lens having a spherical surface and a cylindrical surface. Further, the spherocylindrical lens is defined, according to Section 3.13.1, as a spectacle lens which combines a paraxial, parallel beam of light in two individual, mutually perpendicular focal lines, whereby the spectacle lens has an apex refractive power only in the two main sections. Further, the term "apex refractive power" is, according to Section 3.10.7, defined as a reciprocal value of the width of the paraxial section. As further defined in Section 3.13.2, the term "main section" relates to one of two perpendicular meridians of the spectacle lens having an astigmatic effect being parallel to the two focal lines. Herein, the term "astigmatic effect" corresponds to an "astigmatic difference" which is defined in Section 3.13.6 as a difference between a value of the apex refractive power in the second main section and the value of the apex refractive power in the first main section. Further, the "cylindrical power" refers, according to Section 3.13.7, to an algebraic difference between the refractive values of the main sections, wherein the refractive value of a particular main section being used as a reference is subtracted from the refractive value of the other main section, while the "cylinder axis" indicates according to Section 3.13.8 the direction of the main section of the spectacle lens whose apex refractive index is used as the reference.

As an alternative, L. N. Thibos, W. Wheeler, and D. Horner (1997), Power Vectors: An Application of Fourier Analysis to the Description and Statistical Analysis of Refractive Error, Optometry and Vision Science 74 (6), S. 367-375, propose to approach the description of a spherocylindrical lens from a viewpoint of Fourier analysis of a power profile. They show that the familiar sine-squared law leads naturally to a Fourier series representation with exactly three Fourier coefficients, representing natural parameters of a thin lens. Herein, a constant term corresponds to a mean spherical equivalent (MSE) power, whereas amplitude and phase of the harmonic correspond to the power and axis of a Jackson cross-cylinder (JCC) lens, respectively. Expressing the Fourier series in rectangular form leads to the representation of an arbitrary spherocylindrical lens as sum of a spherical lens and two cross-cylinders, one at axis 0° and the other at axis 45°. The power of these three component lenses may be interpreted as (x, y, z) coordinates of a vector representation of the power profile. The power vector representation of a spherocylindrical lens can be used for numerical and graphical analysis of optometric data for problems involving lens combinations, comparison of different lenses, and statistical distribution of refractive errors.

The method according to the present disclosure is a computer-implemented method. As used herein, the term "computer-implemented method" refers to a method involving at least one programmable device, particularly, be selected from a mobile communication device, a virtual reality device, or an augmented reality device. However, a further kind of programmable device may also be feasible. Herein, the at least one programmable device may, in particular, comprise or have access to at least one evaluation unit, wherein at least one of the features of the method is performed by using at least one computer program. In accordance with the present disclosure, the computer program may be provided on the at least one programmable device, or the at least one mobile communication device may have access to the computer program via a network, such as an in-house network or the internet.

Without restricting the scope of the present disclosure, the corresponding methods and devices are described by using at least one mobile communication device as the at least one programmable device. As generally used, the term "mobile communication device" refers to at least one of a smartphone, a tablet, or a personal digital assistant, which can be carried by the person and, may thus, move together with the person. In general, the at least one mobile communication device comprises at least one screen, at least one camera, and at least one processing unit, wherein a mobile operating system running on the processing unit may be configured to facilitate a use of software, internet, and multimedia functionalities, in particular by using at least one wireless communications protocol, such as Wi-Fi or Bluetooth. Further, the at least one processing unit may comprise the at least one evaluation unit. Further, the at least one mobile communication device may comprise at least one sensor which may, in particular, be selected from at least one of a motion sensor, a gyro sensor, an accelerometer, a proximity sensor, a magnetometer, or a barometer. However, further kinds of sensors may also be conceivable. Further, the at least one mobile communication device may comprise at least one microphone configured to record at least one voice of the person.

According to step a), at least one image is displayed to a person, wherein the at least one image comprises at least one line, wherein the at least one line comprises a plurality of sections, wherein an orientation of each section with respect to an optical axis of the image differs from each other. As used herein, the term "image" refers to a two-dimensional representation or to a three-dimensional representation of the at least one geometric pattern which can act as a stimulus to at least one eye of the person as described below in more detail.

In accordance with the present disclosure, at least one screen as comprised by at least one mobile communication device may, typically, be used for performing step a). In a particularly typical embodiment, the at least one screen may be located in front of the at least one mobile communication device, wherein the at least one mobile communication device can be arranged in a fashion that the at least one screen may face the at least one eye of the person. However, other arrangements in which the at least one mobile communication device may comprise at least one additional screen which may, alternatively or in addition, be used for this purpose, in particular by using at least one additional optical element, such as at least one optical mirror, may also be conceivable the person skilled in the art. In a further arrangement, the screens of more than one mobile communication device can be used in a consecutive or, typically, a simultaneous fashion.

As indicated above, the at least one image as displayed according to step a) comprises at least one line. As generally used, the term "line" refers to a two-dimensional curve having a length which exceeds a lateral extension, typically, by a factor of at least 10, more typical of at least 25, especially of at least 50. Herein, the at least one line may, typically, be a continuous line; however, a dashed line may also be feasible. Further, the at least one line may be black or exhibit at least one color. Further, the at least one line may exhibit a uniform lateral extension, or the lateral extension may vary along the length of the at least one line. Further, the line may exhibit a uniform contrast, or the contrast may vary along the length of the at least one line. Further embodiments of the at least one line may also be feasible.

In particular accordance with the aim of the present disclosure of determining at least one astigmatic effect of the at least one eye of the person, the line has a form which comprises a plurality of sections, wherein an orientation of each section with respect to an optical axis of the image differs from each other. As a result of its form, the line is, therefore, configured to present a plurality of possible linear orientations to the eye of the person. This form is in particular contrast to a stripe pattern having a plurality of sections, wherein the orientation of each section is identical with respect to each other. In an exemplary embodiment, the at least one line may be a curve as denoted by the term a "paraboloid line" by Murphy (2002), see above. However, it is emphasized here that a different curve apart from the paraboloid line can also be used for the purposes of the present disclosure as long as the orientations of the sections of at least one line differ from each other. As described below in more detail, a single line may, in general, be sufficient for at least some of the purposes of the present disclosure.

In an exemplary embodiment, the at least one image as displayed according to step a) comprises two individual lines, wherein each individual line may comprise the same or a different plurality of sections, wherein the orientation of each section with respect to an optical axis of the image may, again, differ from each other, in particular, to be able to present various, typically all, possible linear orientations to the eye of the person. More particular, the two individual lines may be presented in the image in a fashion that they produce an arrow having an apex and a base. As described by Raubitschek (1930 and 1952), see above, in more detail, the two individual lines may approach each other and become parallel to each other at the apex of the arrow in a manner that two individual lines point in opposite directions at the base of the arrow. This kind of arrangement of the two individual lines is denoted by Murphy (2002), see above, using the term "Raubitschek arrow." While according to Murphy (2002) and Raubitschek (1930 and 1952) the two lines may approach, but without touching, and become parallel to each other near the apex of the arrow, it is, in accordance with the present disclosure, rather advantageous that the two parallel lines may touch each other near the apex of the arrow, in particular, since this embodiment may facilitate an assessment of a symmetry of at least one of sharpness, darkness, blackness, or contrast appearance of the two individual lines. In addition, the Raubitschek arrow may comprise a central point, the presentation of which may be enhanced by a reticle, also denoted as "Bannon's cross," which has, primarily, been devised to assist in determining the at least one power of the at least one astigmatic effect, in particular, by facilitating a fixation of the at least one line by the at least one eye of the person and by supporting a rotation of the at least one line as described below in more detail. In addition, the central point may be surrounded by an enclosing figure, such as circle surrounding the central point, which could provide further assistance for these purposes. As further defined by Murphy (2002), the term "central point" refers to a location between the two individual lines at which the arrow can be bisected. More generally, the term "central point" refers to a location which provides a center of gravity for the at least one line. However, it is emphasized here that the arrangement of the two individual lines according to the present disclosure is not limited to the Raubitschek arrow but also allows using a further kind of lines.

In a particularly typical embodiment, the at least one mobile communication device may be configured to have access to the at least one image as displayed during step a) or to a reference thereto. As used herein, the term "access" refers to a configuration of the at least one mobile communication device which enables it to receive the at least one image that has been displayed during step a) or a piece of information which is configured to recover the at least one image as displayed during step a) upon request. For this purpose, the at least one image may be stored, typically in at least one of a pixel-wise manner or in a compressed fashion, in at least one storage unit as further comprised by the at least one mobile communication device or attached to the at least one mobile communication device. The at least one piece of information may be or comprise at least one specification which can be configured to recover the at least one image. By way of example, the at least one piece of information may be selected from at least one specification and at least one parameter of the at least one line. Herein, the specification may, in particular, provide the type of the at least one line, such as at least one paraboloid line, while the parameter may be at least one value related to the selected type of line.

As an alternative, a reference to the at least one image as displayed during step a) may be stored in the at least one storage unit as comprised by the at least one mobile communication device or attached to the at least one mobile communication device. As used herein, the term "reference" refers to at least one piece of information which allows providing the at least one image upon demand as expressed by a computer program which runs on at least one of the at least one mobile communication device or on at least one server communicating with the mobile communication device. Herein, the at least one image may be stored on the at least one mobile communication device or on the at least one server. Further, the at least one piece of information which provides access to the at least one image may be at least one code which may be assigned to the at least one image for reference, such as a numeric or an alphanumeric value assigned to the at least one image, typically in a unique fashion.

According to step b), at least one reaction of the person to the at least one image as displayed to the person according to step a) is recorded over time. Herein, the at least one image acts as a stimulus to the at least one eye of the person, whereby a response of the person is initiated, wherein the response of the person is, generally, referred to by the term "reaction." As generally used, the term "recording" or any grammatical variation thereof relates to any kind of recognizing the reaction of the person, either by observing the behavior of the person or, alternatively or in addition, by monitoring a monitoring signal, in particular an electronic signal, which can be provided by at least one input unit designated for this purpose. In particular, the measuring signal can be provided to an evaluation unit which is configured to detect a point in time at which the reaction of the person occurs to at least one the at least one image being displayed at the point in time. In particular, the reaction of the person can be recorded simultaneously for both eyes or, alternatively or in addition, in a consecutive fashion. For the latter, one of the eyes of the person can, for example, be covered, in particular, initiated by a supervisor or, typically, a corresponding menu in the mobile communication device.

The reaction of the person can be recorded by using an input unit, wherein the input unit is configured to record a reaction of a person to the at least one image over time. As generally used, the term "input unit" refers to a device which is configured to monitor an occurrence of an event by providing or interrupting a monitoring signal at a point in time at which the event occurs. In particular, the input unit can be a keyboard comprising at least one button or key to be pressed by the person in order to express the reaction. Herein, the keyboard may be at least one of a real keyboard or, typically, a virtual keypad as comprised by at least one touch-sensitive screen of the mobile communication device. As an alternative or in addition, the input unit can comprise at least one microphone which may be configured to receive a sound as produced by the person to indicate the desired reaction.

In an exemplary embodiment, the at least one mobile communication device may comprise at least one screen which displays a visual leveling cue including a guideline to assist the person in maintaining a constant level relationship between the at least one mobile communication device and the person while the at least one reaction of the person is recorded according to step b). As generally used, the term "visible leveling cue" refers to an indicator presented to the person in a visual fashion in order to provide to the person at least one piece of information about the constant level relationship between the at least one mobile communication device and the person. Herein, the constant level relationship between the at least one mobile communication device and the person may, in particular, refer to at least one of a distance or a relative orientation between the at least one mobile communication device and the person, especially the eye of the person. As further used herein, the term "guideline" refers to at least one further piece of information presented to the person, typically in a visual, acoustic or tactile fashion, which provides at least one of a recommendation to the person or a confirmation of an action performed by the person, specifically during the at least one reaction of the person.

As a further alternative or in addition, the reaction of the person can be recorded by using a monitoring device, wherein the monitoring device is configured to monitor the behavior of the person. In particular, at least one camera can be used for recording at least one gesture of the person, wherein the reaction of the person can be observed by evaluating the at least one gesture of the person, in particular, by using the at least one evaluation device. For this purpose, the at least one camera of the at least one mobile communication device can be used. In particular, the at least one camera may be at least one of a front camera or a rear camera as comprised by the at least one mobile communication device. In a particularly typical embodiment, the at least one front camera located in front of the at least one mobile communication device may be used, wherein the at least one mobile communication device can be arranged in a fashion that the at least one front camera may face the at least one eye of the person. However, other arrangements in which the at least one rear camera of the at least one mobile communication device may, alternatively or in addition, be used for this purpose, in particular by using at least one additional optical element, such as at least one optical mirror, may also be conceivable the person skilled in the art. In a further arrangement, the cameras of more than one mobile communication device can be used in a consecutive or, typically, a simultaneous fashion.

According to step c), the at least one value for the at least one astigmatic effect of the at least one eye of the person is determined by evaluating the at least one reaction of the person at the point in time. As generally used, the term "determining" or any grammatical variation thereof refers to a process of generating at least one representative result, such as a plurality of representative results. As further used herein, the term "evaluating" or any grammatical variation thereof refers to applying at least one algorithm to extract at least one piece of information from the at least one reaction of the person at the point in time to the at least one image. The at least one algorithm may be configured to determine the at least one value for the at least one astigmatic effect of the at least one eye of the person by evaluating the type of reaction to the at least one image according to a scheme. However, other ways of determining the at least a property of the at least one line may also be feasible.

The determination of the at least one value for at least one astigmatic effect of the at least one eye of the person may be performed in accordance with a predefined scheme, however, artificial intelligence, in particular machine learning, may also be applied, especially by using a neuronal network. As generally used, the term "machine learning" refers to a process applying artificial intelligence to automatically generate a statistical model for classification or regression. A machine learning algorithm configured to generate the desired model based on a large number of training data sets can, typically, be used. Herein, the machine learning algorithm can be a supervised algorithm or a self-learning algorithm. The machine learning algorithm can use and/or comprise a neural network, which may, typically, be developed into a trained neural network by using the at least one training data set. The neural network may comprise at least one element selected from hierarchical decision trees, Hough forest, regression forest, Convolutional Neural Network (CNN), Deep Neural Network (DNN) Residual Neural Network, Pixel-wise Voting, Pixel-wise Fusion Network, Deep learning. Alternatively or additionally, the use of at least one other artificial intelligence method, typically a kernel method, especially a Support Vector Machine (SVM), may also be possible.

In a particularly typical embodiment, the at least one mobile communication device may, in addition, be configured to perform step c). For this purpose, the at least one mobile communication device may comprise at least one evaluation unit, wherein the at least one evaluation unit may be configured to determine the at least one value for the at least one astigmatic effect of the at least one eye of the person by evaluating the type of reaction to the at least one image. Alternatively or in addition, the at least one mobile communication device may be configured to perform step c) by using at least one communication interface as further comprised by the at least one mobile communication device. In this embodiment, the at least one communication interface may be configured to exchange data with at least one server, wherein the at least one server, which is not comprised by the at least one mobile communication device, is configured to determine the at least one value for the at least one astigmatic effect of the at least one eye of the person by evaluating the type of reaction to the at least one image and to, typically, provide the at least one value to the evaluation unit of the at least one mobile communication device.

As generally used, the term "communication interface" refers a transmission channel which is designated for a transmission of data. Herein, the communication interface may be arranged as a unidirectional interface which is configured to forward at least one piece of data into a single direction, either from the at least one evaluation unit to the server, or from the server to the at least one evaluation unit. Alternatively, the communication interface may be arranged as a bidirectional interface which is configured to forward at least one piece of data into one of two directions, from the at least one evaluation unit to the server, or vice versa. Thus, a particular bidirectional interface can, as an alternative, be replaced by two individual unidirectional interfaces which are configured for data transmission in an opposite direction with respect to each other. For a purpose of data transmission, the communication interface may, typically, comprise a wireless element, which may, by way of example, operate by using at least one wireless communications protocol, such as Wi-Fi or Bluetooth. However, further kinds of communication interfaces may also be feasible.

As further generally used, the term "server" refers to a device which is configured to provide resources to a further device, typically denoted as "client," wherein the "resources," in particular, comprise at least one of computing power, such as for running at least one computer program; or data storage capacity, such as for storing at least one piece of data. By way example, a client can run a single computer program or store pieces of data distributed across multiple servers, while a single server can serve multiple clients with regard to at least one of program execution and storage requirement. While the term "server" refers to a device that is arranged within a local network, the term "cloud server" relates to a kind of server that is accessible on demand by the client via internet. As a result, neither a location of the cloud server nor a direct active management of the cloud server is accessible to the client.

In accordance with the present disclosure, the reaction of the person to the at least one image comprises indicating on the at least one line a position which refers to at least one transition from the first appearance of the at least one line to the person into the second appearance of the at least one line to the person, or vice versa, wherein the second appearance of the at least one line to the person differs from the first appearance of the at least one line to the person. As generally used, the term "appearance of the at least one line" refers to a kind of recognition of the at least one line, especially of the at least one line as whole, by the eye of the person which is, initially, investigated whether it may exhibit at least one astigmatic effect at all or not. In one case, in which the eye of the person recognizes the at least one line, especially the at least one line as whole, without any shadow along the line demonstrates that the eye of the person is free from at least one astigmatic effect. In a further case, in which the eye of the person recognizes a shadow at at least one portion along the at least one line demonstrates that the eye of the person exhibits at least one astigmatic effect.

In particular, the line as recognized by the eye of the person along the length of at least one line can be divided into at least two different portions, a first portion in which the line exhibits the first appearance to the eye of the person and at least one adjacent second portion in which the line exhibits the second appearance to the eye of the person, mainly depending on an individual impression of the person, in particular, based on a kind and power of astigmatism and personal experience. As used herein, the term "first appearance" refers to a type of recognition of the corresponding portion of the line by the eye of the person which allows recognizing the borders of the corresponding portion of the line in a fashion in which the eye can differentiate first areas in the image which belong to the line and second areas which are located outside the line, in particular at least one of a sharp, a dark, a black, or a high contrast appearance of the at least one line to the person. In contrast hereto, the term "second appearance" refers to a further type of recognition of the at least one corresponding portion of the line by the eye of the person which impedes recognizing the borders of the corresponding portion of the line in a fashion in which the eye cannot differentiate first areas in the image which belong to the line and second areas which are located outside the line, in particular at least one of a blurred, a bright, a gray, or a low contrast appearance of the at least one line to the person. For further details and examples hereto, reference can be made to the exemplary embodiments as presented below.

As further used herein, the term "transition" indicates at least one position on the at least one line in which a first portion in which the line exhibits the first appearance to the eye of the person terminates and at least one adjacent second portion in which the line exhibits the second appearance to the eye of the person commences, or vice versa. Herein, the position of the at least one transition along the line is related to the at least one astigmatic effect as exhibited by the eye of the person. As indicated above, the line as used in connection with the present disclosure has a form which comprises a plurality of sections, wherein the orientation of each section with respect to an optical axis of the image differs from each other in a fashion that the line, thus, presents various, typically all, possible linear orientations to the eye of the person. As a result, the position of at least one transition from the first appearance into the second appearance as observed by the eye of the person relates to a change of the orientation of the at least one line. As a result, the at least one value for the at least one astigmatic effect is, in further accordance with the present disclosure, determined from the position of the at least one transition on the at least one line.

In general, indicating the position of the at least one transition on the at least one line from the first appearance to the person into the second appearance to the person, or vice versa, can be performed in an arbitrary fashion. In a particularly typical embodiment, indicating the position of the at least one transition on the at least one line from the first appearance to the person into the second appearance to the person, or vice versa, can comprise recording the reaction of the person to the at least one image at at least one point in time, according to step b), by performing at least one of:

pointing at the position of the at least one transition on the at least one line on at least one touch-sensitive screen of at least one mobile communication device by using at least one finger of the person;

determining at least one gesture movement of the person by using at least one of a camera or a motion sensor of the at least one mobile communication device;

moving at least one geometrical figure over the at least one touch-sensitive screen of the at least one mobile communication device by using the at least one finger of the person;

moving the at least one geometrical figure over the at least one screen of the at least one mobile communication device by using a voice of the person.

However, further alternatives may also be conceivable.

Herein, the at least one touch-sensitive screen of the mobile communication device on which the at least one line is displayed can, typically, be used for indicating the position of the at least one transition on the at least one line by using the at least one finger of the person. For this purpose, a corresponding menu in the mobile communication device may be configured to request the person to perform accordingly. Alternatively or in addition, the at least one of the camera or the motion sensor of the mobile communication device can, typically, be used for determining the at least one gesture movement of the person. As generally used, the term "gesture" refers to a behavior of the person which addresses the mobile communication device, in particular a view of the person towards the at least one screen of the mobile communication device which displays the at least one line. Herein, a movement of the gesture, especially of the view, of the person could be used in an algorithm configured to determine the position of the at least one transition.

As a further alternative, the at least one geometrical figure may be moved over the at least one touch-sensitive screen of the mobile communication device by using the at least one finger of the person. Herein, the at least one geometrical figure may, typically, comprise a horizontal bar which can be moved by using the at least one finger of the person over the at least one touch-sensitive screen until it may rest in a place which may indicate the position of the at least one transition. Alternatively or in addition, the at least one geometrical figure may be moved over the at least one screen by using a sound as produced by the person which may be recorded by the at least one microphone as comprised by the mobile communication device.

In particular, determining the at least one value for the at least one astigmatic effect of the at least one eye of the person according to step c) may comprise at least one of the following sub-steps:
  (i) determining at least one value for at least one orientation of an axis of the astigmatic effect of the at least one eye of the person from at least two transitions;
  (ii) determining at least one value for at least one power of the astigmatic effect of the at least one eye of the person.

In particular, the present method may be used for determining at least one value for
  both the at least one orientation of the axis and the at least one power, wherein the at least one orientation of the axis according to sub-step (i) may, typically, be determined after or, alternatively, prior to the at least one power according to sub-step (ii); or
  only the at least one power
of the astigmatic effect of the at least one eye of the person.

With respect to sub-step (i), the at least one value for the at least one orientation of the axis of the astigmatic effect according to sub-step (i) may, typically, be determined by performing a rotation of the at least one line by at least one angular value around a central point of the at least one line. As generally used, the term "rotation" refers to a continuous or step-wise alteration of an angular value of the presentation of the at least one line to the at least one eye of the person. For a definition of the term "central point," reference can be made to the description above. In a particularly typical embodiment, step a) may, typically, further comprise performing a rotation of the at least one image comprising two individual lines, in particular by using a respective algorithm, by at least one angular value, in particular around the central point of the two individual lines, until the two individual lines are, according to step b), indicated by the person to appear as symmetrical with respect to at least one of sharpness, darkness, blackness, or contrast to the person. In particular, the rotation of the two individual lines can be performed by rotating the at least one image as displayed during step a), which comprises the representation of the two individual lines. For a purpose of providing the response, the person can actively stop the rotation of the at least one continuously or step-wise rotating line, specifically by pressing a button or a key, or by producing a sound as described above or below in more detail. Alternatively or in addition, the rotation of the at least one line may be performed by rotating the at least one screen as comprised by the mobile communication device which displays the at least one image during step a).

Independently of the way the rotation of the at least one image may be performed, the at least one value for the at least one orientation of the axis of the astigmatic effect can be determined from the at least one angular value of the rotation of the two individual lines at the point in time, wherein the at least one angular value as used for this purpose corresponds to at least one angular value at which the reaction of the person according to step b) indicates at the point in time that the person considers the two individual lines as symmetrical with respect to at least one of sharpness, darkness, blackness, or contrast.

With respect to sub-step (ii), the at least one value for the at least one orientation of the axis of the astigmatic effect according to sub-step (i) may, in an exemplary embodiment, be determined prior to the at least one value for the at least one power of the astigmatic effect according to sub-step (ii). In particular, the at least one line which may be used for determining the at least one value for the at least one power of the astigmatic effect according to sub-step (ii) may be displayed according to step a) in an orientation which corresponds to the at least one value for the at least one orientation of the axis of the astigmatic effect as determined before according to sub-step (i). As particularly used is this context, the term "corresponding" or any grammatical variation thereof may refer to a parallel arrangement of both orientations, wherein, however, an arrangement in which both orientations differ by an angle of not more than 1°, not more than 2°, not more than 5°, not more than 10°, not more than 20°, or not more than 30°, may also be advantageous. The latter arrangement may, in particular, allow altering the appearance of the first and the at least one adjacent second portion as defined above within two individual lines, i.e., the first portion in which the at least one line exhibits the first appearance to the eye of the person and the at least one adjacent second portion in which the at least one line exhibits the second appearance to the eye of the person, from which the at least one power of the astigmatic effect according to sub-step (ii) can be determined by taking into account the different appearance of the two lines under the actual angle of presentation of the two lines to the at least one eye of the person according to step a). Herein, the at least one value for the at least one power of the astigmatic effect may, typically, be determined from a ratio of a first length of the first portion in which the at least one line exhibits the first appearance to the eye of the person versus a second length of the at least one adjacent second portion in which the at least one line exhibits the second appearance to the eye of the person. In general, the ratio as defined herein assumes a smaller value for an increasing value of the at least one power of the astigmatic effect. As illustrated below with in more detail, the smaller value of the ratio indicates a larger power of the astigmatic effect while a larger value of the ratio indicates a smaller power of the astigmatic effect in the at least one eye of the person.

In an alternative embodiment, the at least one value for the at least one power of the astigmatic effect according to sub-step (ii) may be determined without prior determining the at least one value for the at least one orientation of the axis of the astigmatic effect according to sub-step (i). In a first alternative, the at least one value for the at least one orientation of the axis of the astigmatic effect may be estimated or may be known from a prior measurement thereof, whether according to sub-step (i) as used herein or not. In a further alternative, as described below with respect to the exemplary embodiments in more detail, wherein the orientation of the axis of the astigmatic effect is not known, at least two positions of two different transition may be determined by the user. Herein, the position of a first transition along the at least one line from the first appearance to the second appearance and the position of a second transition along the at least one line from the first appearance to a further second appearance may be indicated by the user. In this embodiment, step c) may, typically, comprise determining the at least on power and the at least axis of at least one astigmatic effect from the length of the portion of the at least one line exhibiting the first appearance to the person between the positions of the two transitions and from a location of a central point on the portion of the at least one line. This alternative embodiment can be repeated on a second line as comprised by the image as displayed according to step a). For further details, reference be made to the exemplary embodiments as described below.

In a further aspect, the present disclosure refers to a computer program which comprises instructions which, when the program is executed by a computer, cause the computer to carry out the method for determining at least one astigmatic effect of at least one eye of a person using at least one mobile communication device according to the present disclosure. For this purpose, a computer program may comprise instructions which can be provided by means of a computer program code which are capable of performing any or all of the steps of the methods as described elsewhere herein and, thus, to establish determining the astigmatic effect of the at least one eye of a person when implemented on a data processing unit as comprised by the at least one mobile communication device.

In a further aspect, the present disclosure relates to a method for producing at least one spectacle lens for at least one eye of a person. As generally, the producing of the at least one spectacle lens comprises processing at least one lens blank by adjusting at least one optical parameter of the at least one spectacle lens, wherein the processing of the lens blank is based on instructions which are configured to compensate the at least one refractive error, in particular of the at least one astigmatic effect, of the at least one eye of a person as described in the prior art. According to the present disclosure, the determining of the at least one astigmatic effect of the at least one eye of the person comprises applying the method for determining at least one refractive astigmatic effect of at least one eye of a person according to the present disclosure.

For further details concerning the computer program or the method for producing at least one spectacle lens, reference may be made to the method for determining at least one astigmatic effect of at least one eye of a person using at least one mobile communication device as disclosed elsewhere herein.

In a further aspect, the present disclosure relates to a device for determining at least one astigmatic effect of at least one eye of a person. According to the present disclosure, the device comprises:
  at least one screen, wherein the at least one screen is configured to display at least one image to at least one eye of a person, wherein the at least one image comprises at least one line, wherein the at least one line comprises a plurality of sections, wherein an orientation of each section with respect to an optical axis of the image differs from each other;
  at least one input unit, wherein the input unit is configured to record at least one reaction of the person to the at least one image at at least one point in time; and
  at least one evaluation unit, wherein the at least one evaluation unit is configured to determine at least one value for at least one astigmatic effect of at least one eye of the person by evaluating the at least one reaction of the person at the point in time, or wherein the at least one evaluation unit comprises at least one communication interface configured to exchange data with at least one server, wherein the at least one server is configured to determine at least one value for at least one astigmatic effect of at least one eye of the person by evaluating the at least one reaction of the person at the point in time,
wherein the at least one input unit is configured to record the at least one reaction of the person to the at least one image indicating a position on the at least one line, wherein the position on the at least one line refers to at least one transition from a first appearance of the at least one line to the person into a second appearance of the at least one line to the person, or vice versa, wherein the second appearance of the at least one line to the person differs from the first appearance of the at least one line to the person, wherein at least one evaluation unit is configured to determine the at least one value for the at least one astigmatic effect from the position of the at least one transition on the at least one line.

In an exemplary embodiment, the device for determining at least one astigmatic effect of at least one eye of a person may, further comprise, at least one of:
  at least one of a camera or a motion sensor configured to determine at least one gesture movement of the person;
  at least one touch-sensitive screen configured to determine a position of the at least one transition on the at least one line by recoding a touching of at least one finger of the person;
  at least one microphone configured to determine a position of the at least one transition on the at least one line by recoding a voice of the person;
  a distance meter, wherein the distance meter is configured to determine at least one distance;
  at least one holding unit attached to the at least one mobile communication device, wherein the at least one holding unit is configured to maintain a position of the at least one mobile communication device.

For the term "mobile communication device," reference can be made to the definition above.

As indicated above, the at least one camera configured to capture the at least one image may, specifically, be selected from at least one of a front camera or a rear camera as comprised by the at least one mobile communication device, wherein the at least one front camera may, especially, be typical. Further, the at least one camera and the at least one evaluation unit of the at least one mobile communication device can, jointly, be used as the distance meter by being configured to determine the at least one distance between the at least one camera and the at least one eye of the person.

In an exemplary embodiment, the at least one screen may be further configured to display a rotation of the at least one line by at least one angular value, in particular around a central point of the two individual lines. Alternatively or in addition, the at least one mobile communication device may comprise at least one gyro sensor configured to determine at least one orientation of the two individual lines in space and, therefrom the rotation of the at least one line by the at least one angular value, in particular around the central point of the two individual lines. In this embodiment, the at least one input unit may, typically, be configured to record the at least one reaction of the person at the at least one point in time when two individual lines appear symmetrical with respect to at least one of sharpness, darkness, blackness, or contrast to the person, and the at least one evaluation unit may, further, be configured to determine the at least one value for at least one orientation of an axis of the astigmatic effect from the angular value of the rotation of the two individual lines at the at least one point in time.

In an exemplary embodiment, the at least one screen as comprised by the at least one mobile communication device may, further, be configured to display a visual leveling cue including a guideline to assist the person in maintaining a constant level relationship between the at least one mobile communication device and the person, in particular at least one of a distance or a relative orientation between the at least one mobile communication device and the person, especially the eye of the person, while the at least one reaction of the person is recorded. For a purpose of determining the at least one distance between the at least one mobile communication device and the person the distance meter may be used, while for a purpose of determining the at least one relative orientation between the at least one mobile communication device and the person the at least one gyro sensor and the at least one camera may be used.

Alternatively or in addition, further embodiments with respect to the device according to the present disclosure are conceivable.

For further details concerning the device for determining at least one astigmatic effect of at least one eye of a person, reference may be made to the method for determining at least one astigmatic effect of at least one eye of a person as disclosed elsewhere herein.

As a particular advantage of the present disclosure, the methods, the computer program and the device as disclosed herein allow determining the at least one astigmatic effect of at least one eye of a person in comparison with the methods, computer programs and devices as used in the prior art by the person itself or by a further person without requiring neither any particular knowledge of measuring at least one astigmatic effect nor any further device apart from a mobile communication device, in particular a smartphone, which is, typically, available to the person or the further person nowadays. Further, it is not required to place an optical lens exhibiting at least one particular astigmatic effect between the image and the eye of the at least one person for performing the method according to the present disclosure.

The at least one value for the at least one astigmatic effect can, in particular, be used as a reliable starting point for determining the at least one refractive error of the at least one eye of the person. Herein, the at least one value for the at least one astigmatic effect may, in particular, be combined with measurements of at least one of visual acuity, contrast sensitivity, illumination conditions, or screen time. In particular, the measurement results can be used for a purpose of at least one of screening or disease tracking, specifically within a familiar environment to the person. Specifically, the methods, the computer program and the device may be used in a tele-medicine system or in relationship with a tele-medicine system. Further applications are conceivable.

As used herein, the terms "have," "comprise" or "include" or any arbitrary grammatical variations thereof are used in a non-exclusive way. Thus, these terms may refer to both a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

As further used herein, the terms "typically," "more typically," "particularly," "more particularly," or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in this way with other features of the disclosure.

Summarizing, the exemplary embodiments according to the following Clauses are particularly typical within the scope of the present disclosure:

Clause 1: A method for determining at least one astigmatic effect of at least one eye of a person, the method comprising the following steps:
  a) displaying at least one image to at least one eye of a person, wherein the at least one image comprises at least one line, wherein the at least one line comprises a plurality of sections, wherein an orientation of each section with respect to an optical axis of the image differs from each other;
  b) recording at least one reaction of the person to the at least one image at at least one point in time; and
  c) determining at least one value for at least one astigmatic effect of at least one eye of the person by evaluating the at least one reaction of the person at the point in time,
wherein the at least one reaction of the person to the at least one image comprises indicating a position on the at least one line, wherein the position on the at least one line refers to at least one transition from a first appearance of the at least one line to the person into a second appearance of the at least one line to the person, or vice versa, wherein the second appearance of the at least one line to the person differs from the first appearance of the at least one line to the person, wherein the at least one value for the at least one astigmatic effect is determined from the position of the at least one transition on the at least one line.

Clause 2: The method according to the preceding Clause, wherein step c) comprises at least one of the following sub-steps:
  (i) determining at least one value for at least one orientation of an axis of the astigmatic effect of the at least one eye of the person from at least two transitions;
  (ii) determining at least one value for at least one power of the astigmatic effect of the at least one eye of the person.

Clause 3: The method according to the preceding Clause, wherein the at least two transitions are located on the same line or on at least two different lines.

Clause 4: The method according to any one of the two preceding Clauses, wherein the at least one orientation of the axis of the astigmatic effect of the at least one eye of the person according to sub-step (i) is determined after the at least one power of the astigmatic effect of the at least one eye of the person according to sub-step (ii).

Clause 5: The method according to any one of the three preceding Clauses, wherein the at least one orientation of the axis of the astigmatic effect of the at least one eye of the person according to sub-step (i) is determined prior to the at least one power of the astigmatic effect of the at least one eye of the person according to sub-step (ii).

Clause 6: The method according to any one of the four preceding Clauses, wherein the at least one orientation of the axis according to sub-step (i) is estimated or known from a prior measurement thereof.

Clause 7: The method according to any one of the five preceding Clauses, wherein the at least one line is displayed for determining the at least one value for the at least one power of the astigmatic effect of the at least one eye of the person according to sub-step (ii) with the at least one value for the at least one orientation of the axis of the astigmatic effect as determined according to sub-step (i), or estimated or known from a prior measurement thereof.

Clause 8: The method according to any one of the six preceding Clauses, wherein the recording of the at least one reaction of the person to the at least one image at the at least one point in time is implemented through at least one mobile communication device.

Clause 9: The method according to the preceding Clause, wherein the at least one mobile communication device comprises at least one screen which displays a visual leveling cue including a guideline to assist the person in maintaining a constant level relationship between the at least one mobile communication device and the person while the at least one reaction of the person is recorded.

Clause 10: The method according to any one of the two preceding Clauses, wherein the at least one value for the at least one power of the astigmatic effect is determined from a ratio of a first length of a first portion of the at least one line exhibiting the first appearance to the person versus a second length of at least one adjacent second portion of the at least one line exhibiting the second appearance to the person.

Clause 11: The method according to any one of the preceding Clauses, wherein step a) further comprises performing a rotation of the at least one image by at least one angular value.

Clause 12: The method according to the preceding Clause, wherein the rotation of the at least one line is performed by rotating the at least one image as displayed during step a).

Clause 13: The method according to any one of the two preceding Clauses, wherein the rotation of the at least one line is performed by rotating at least one screen displaying the at least one image during step a).

Clause 14: The method according to any one of the preceding Clauses, wherein indicating the position of the at least one transition on the at least one line from the first appearance to the person into the second appearance to the person, or vice versa, according to step b), comprises at least one of:
  pointing at the position of the at least one transition on the at least one line on at least one touch-sensitive screen of at least one mobile communication device by using at least one finger of the person;
  determining at least one gesture movement of the person by using at least one of a camera or a motion sensor of the at least one mobile communication device;
  moving at least one geometrical figure over the at least one touch-sensitive screen of the at least one mobile communication device by using the at least one finger of the person;
  moving the at least one geometrical figure over the at least one screen of the at least one mobile communication device by using a voice of the person.

Clause 15: The method according to any one of the preceding Clauses, wherein step a) comprises displaying two individual lines.

Clause 16: The method according to the preceding Clause, wherein step a) further comprises performing a rotation of the two individual lines by at least one angular value.

Clause 17: The method according to the preceding Clause, wherein the rotation of the two individual lines by the at least one angular value is performed around a central point of the two individual lines.

Clause 18: The method according to the preceding Clause, wherein step a) further comprises performing the rotation of the two individual lines by at least one angular value around the central point of the two individual lines until the two individual lines are, according to step b), indicated by the person at the point in time to appear as symmetrical with respect to at least one of sharpness, darkness, blackness, or contrast to the person.

Clause 19: The method according to the preceding Clause, wherein the at least one value for the at least one orientation of the axis of the astigmatic effect is determined from the at least one angular value of the rotation of the two individual lines at the point in time.

Clause 20: The method according to any one of the five preceding Clauses, wherein the two individual lines form a Raubitschek arrow.

Clause 21: The method according to the preceding Clause, wherein the two individual lines produce an arrow having an apex and a base, wherein the two individual lines become parallel to each other at the apex of the arrow, and wherein the two individual lines point in opposite directions at the base of the arrow.

Clause 22: The method according to the preceding Clause, wherein the two individual lines touch each other at the apex of the arrow.

Clause 23: A computer program comprising instructions which, when the program is executed by a computer, cause the computer to carry out a method for determining at least one astigmatic effect of at least one eye of a person according to any one of the preceding Clauses.

Clause 24: A method for producing at least one spectacle lens for at least one eye of a person, wherein the producing of the at least one spectacle lens comprises processing at least one lens blank by adjusting at least one optical parameter of the at least one spectacle lens, wherein the processing of the lens blank is based on instructions configured to compensate at least one astigmatic effect of the at least one eye of the person, wherein the determining of the at least one astigmatic effect of the at least one eye of the person comprises using the steps of the method according to any one of the preceding Clauses referring to a method for determining the at least one astigmatic effect of the at least one eye of the person.

Clause 25: A device for determining at least one astigmatic effect of at least one eye of a person, the device comprising:
  at least one screen, wherein the at least one screen is configured to display at least one image to at least one eye of a person, wherein the at least one image comprises at least one line, wherein the at least one line comprises a plurality of sections, wherein an orientation of each section with respect to an optical axis of the image differs from each other;
  at least one input unit, wherein the input unit is configured to record at least one reaction of the person to the at least one image at at least one point in time; and at least one evaluation unit, wherein the at least one evaluation unit is configured to determine at least one value for at least one astigmatic effect of at least one eye of the person by evaluating the at least one reaction of the person at the point in time, or wherein the at least one evaluation unit comprises at least one communication interface configured to exchange data with at least one server, wherein the at least one server is configured to determine at least one value for at least one astigmatic effect of at least one eye of the person by evaluating the at least one reaction of the person at the point in time, wherein the at least one input unit is configured to record the at least one reaction of the person to the at least one image indicating a position on the at least one line, wherein the position on the at least one line refers to at least one transition from a first appearance of the at least one line to the person into a second appearance of the at least one line to the person, or vice versa, wherein the second appearance of the at least one line to the person differs from the first appearance of the at least one line to the person, wherein at least one evaluation unit is configured to determine the at least one value for the at least one astigmatic effect from the position of the at least one transition on the at least one line.

The device according to the preceding Clause, wherein the at least one evaluation unit or the at least one server is configured to perform step c) according to at least one of the following sub-steps:
(i) determining at least one value for at least one orientation of an axis of the astigmatic effect of the at least one eye of the person from at least two transitions;
(ii) determining at least one value for at least one power of the astigmatic effect of the at least one eye of the person.

Clause 26: The device according to the preceding Clause, wherein the at least one screen is configured to display the at least one line for determining the at least one value for the at least one power of the astigmatic effect of the at least one eye of the person with the at least one value for the at least one orientation of the axis of the astigmatic effect.

Clause 27: The device according to any one of the two preceding Clauses, wherein the at least one evaluation unit or the at least one server is configured to determine the at least one value for the at least one power of the astigmatic effect from a ratio of a first length of a first portion of the at least one line exhibiting the first appearance to the person versus a second length of at least one adjacent second portion of the at least one line exhibiting the second appearance to the person.

Clause 28: The device according to the preceding Clause, wherein the at least one screen is further configured to display a rotation of the at least one line by at least one angular value.

Clause 29: The device according to the preceding Clause, wherein the at least one screen is further configured to display the rotation of the at least one line by at least one angular value.

Clause 30: The device according to any one of the preceding Clauses referring to a device, wherein at least one gyro sensor is configured to determine at least one orientation of the at least one line in space and, therefrom the rotation of the at least one line by the at least one angular value.

Clause 31: The device according to any one of the preceding Clauses referring to a device, wherein the at least one input unit is configured to record the at least one reaction of the person at the at least one point in time when two individual lines appear symmetrical with respect to at least one of sharpness, darkness, blackness, or contrast to the person.

Clause 32: The device according to any one of the preceding Clauses referring to a device, wherein the at least one evaluation unit is further configured to determine at least one value for at least one orientation of an axis of the astigmatic effect from the angular value of the rotation of the at least one line at the at least one point in time.

Clause 33: The device according to any one of the preceding Clauses referring to a device, further comprising at least one of a camera or a motion sensor configured to determine at least one gesture movement of the person.

Clause 34: The device according to any one of the preceding Clauses referring to a device, further comprising at least one touch-sensitive screen configured to determine a position of the at least one transition on the at least one line by recoding a touching of at least one finger of the person.

Clause 35: The device according to any one of the preceding Clauses referring to a device, further comprising at least one microphone configured to determine a position of the at least one transition on the at least one line by recoding a voice of the person.

Clause 36: The device according to any one of the preceding Clauses referring to a device, wherein the device is or comprises at least one mobile communication device.

Clause 37: The device according to the preceding Clause referring to a device, wherein the at least one mobile communication device comprises at least one distance meter, wherein the at least one distance meter is configured to determine at least one distance.

Clause 38: The device according to any one of the two preceding Clauses, wherein the at least one screen as comprised by the at least one mobile communication device is further configured to display a visual leveling cue including a guideline to assist the person in maintaining a constant level relationship between the at least one mobile communication device and the person while the at least one reaction of the person is recorded.

Clause 39: The device according to any one of the three preceding Clauses, further comprising at least one holding unit attached to the at least one mobile communication device, wherein the at least one holding unit is configured to maintain a position of the at least one mobile communication device.

BRIEF DESCRIPTION OF THE DRAWINGS

Further optional features and embodiments of the present disclosure are disclosed in more detail in the subsequent description of exemplary embodiments, typically in conjunction with the dependent claims. Therein, the respective optional features may be realized in an isolated fashion as well as in any arbitrary feasible combination, as the skilled person will realize. It is emphasized here that the scope of the disclosure is not restricted by the exemplary embodiments.

The disclosure will now be described with reference to the drawings wherein.

DESCRIPTION OF EXEMPLARY EMBODIMENTS

Figure 1:
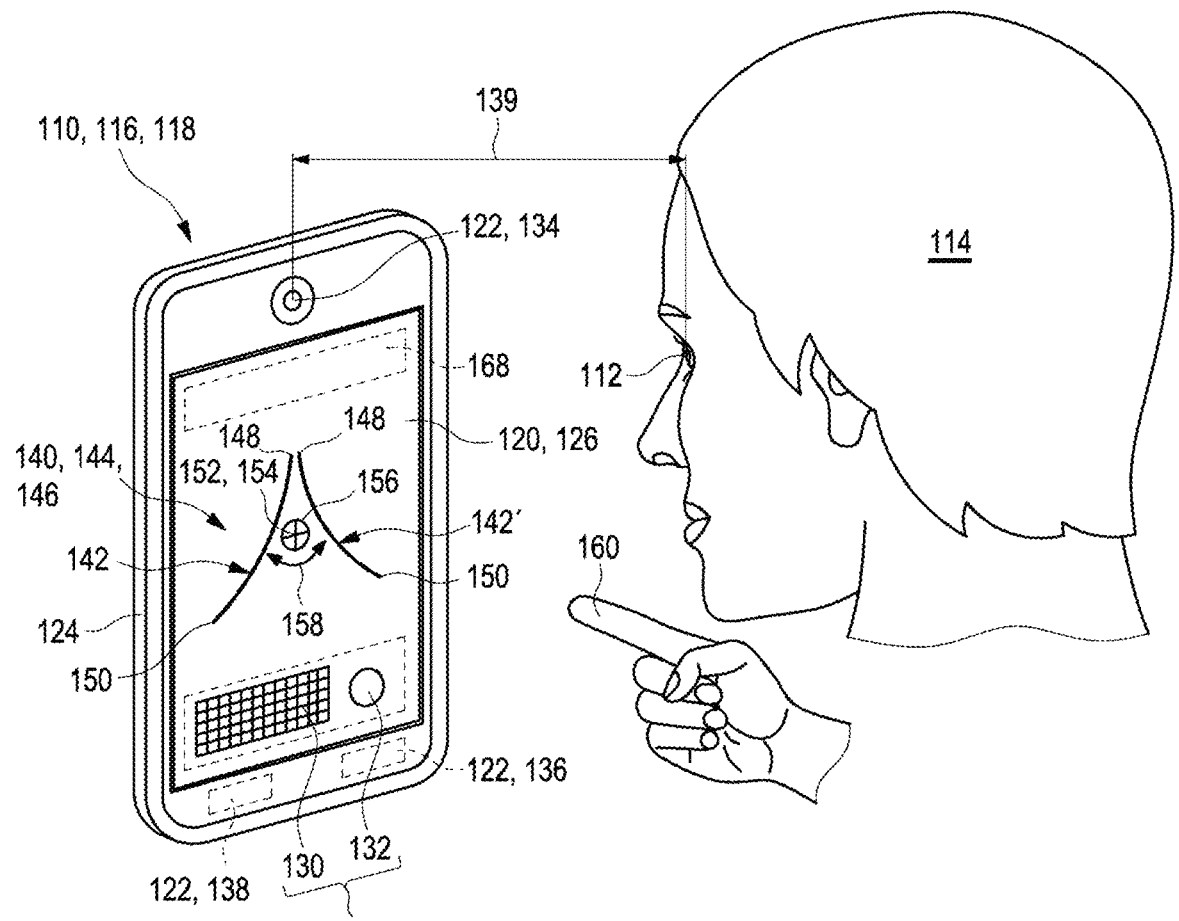
FIG. 1 illustrates an exemplary embodiment of a device for determining at least one astigmatic effect of an eye of a person according to the present disclosure.

FIG. 1 illustrates an exemplary embodiment of a device 110 for determining at least one astigmatic effect of an eye 112 of a person 114 using a mobile communication device 116. Herein, the at least one astigmatic effect of both eyes 112 of the person 114 can, typically, be determined in a consecutive fashion. As schematically depicted, the exemplary device 110 of FIG. 1 comprises—without limiting the scope of the disclosure—a smartphone 118 as a typical example of the mobile communication device 116. Herein, the smartphone 118 comprises a screen 120, an input unit 122, and an evaluation unit 124. As illustrated there, the screen 120 as used herein is a touch-sensitive screen 126, while the input unit 122 comprises an input area 128 having a virtual keypad 130 and a button 132, a camera 134, a motion sensor 136 and a microphone 138. Herein, the camera 134 and the evaluation unit 124 of the smartphone 118 can, jointly, be used as a distance meter by being configured to determine at least one distance 139 between the camera 134 and the eye 112 of the person 114. Alternatively or in addition, the smartphone 118 may, further, comprise at least one distance meter (not depicted here) configured to determine the distance 139 between the eye 112 of the person 114 and the smartphone 118. Further, a holding unit (not depicted here) may be configured to maintain the smartphone 118 in a desired position, in particular, to increase precision accuracy, and reliability of the determination of the at least one astigmatic of the eye 112.

Figure 2:
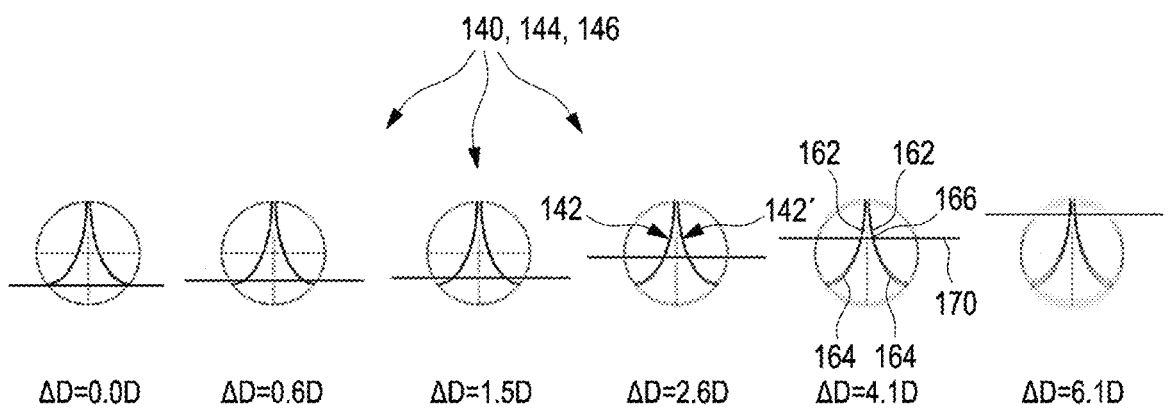
FIG. 2 illustrates a typical method of determining a value for a power of the astigmatic effect.
Figure 3:
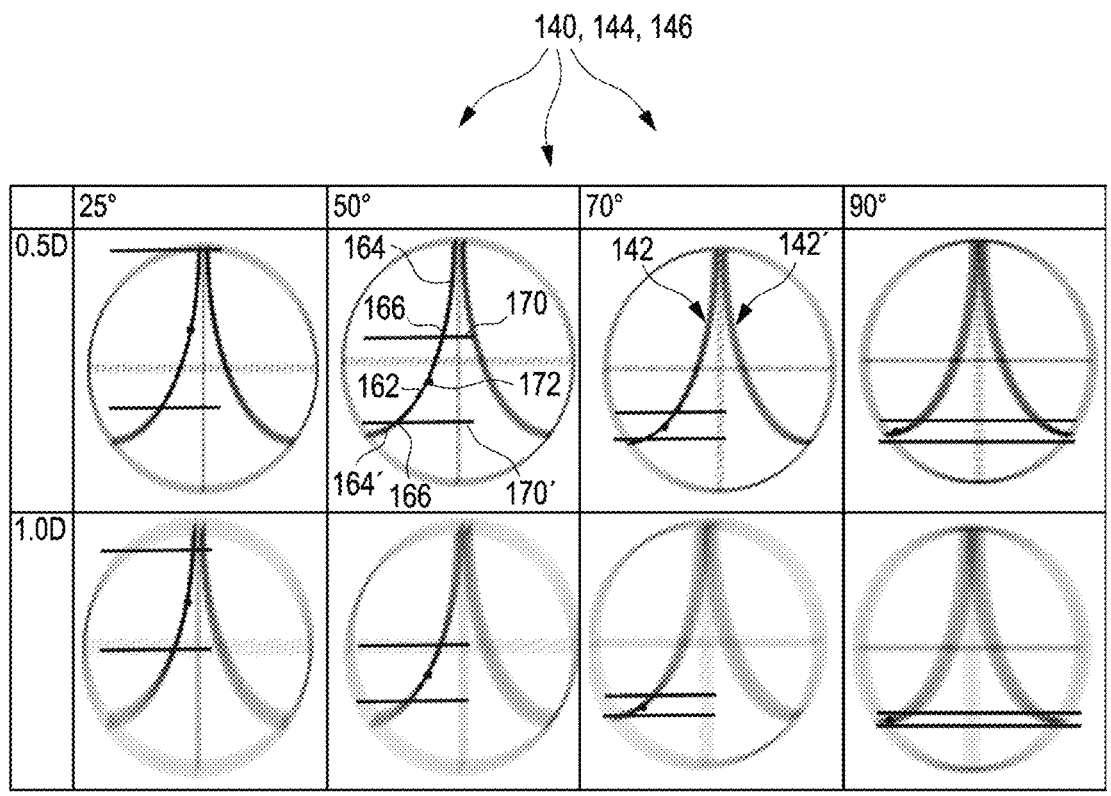
FIG. 3 illustrates a typical method of determining the value for the power of the astigmatic effect.

As further illustrated in FIG. 1, the screen 120 is configured to display one or more images 140 to the eye 112 of the person 114. As schematically depicted there, the image 140 comprises two individual lines 142, 142', each individual line 142, 142' having a form which comprises a plurality of sections, wherein an orientation of each section differs from each other. As a result of its form, each individual line 142, 142' is, therefore, configured to present a plurality of possible linear orientations to the eye 112 of the person 114. As schematically depicted in FIGS. 1 to 3, the two individual lines 142, 142' which are displayed on the screen 120 may, typically, assume the form of a Raubitschek arrow 144. In the Raubitschek arrow 144, the two individual lines 142, 142' produce, as described by Murphy (2002), cited above, an arrow 146 having an apex 148 and a base 150, wherein the two individual lines 142, 142' approach and become parallel to each other at the apex 148 of the arrow 146, and wherein the two individual lines 142, 142' point in opposite directions at the base 150 of the arrow 146. In a particularly typical embodiment, the two parallel individual lines 142, 142' may touch each other near the apex 148 of the arrow 146, thereby in particular, facilitating an assessment of the symmetry of at least one of sharpness, darkness, blackness, or contrast appearance of the two individual lines 142, 142' to the person 114. However, an image (not depicted here) which presents only a single line 142 or 142' may also be feasible.

As described above in more detail, the two individual lines 142, 142' may, as depicted here, be, typically, continuous lines; however, dashed lines may also be feasible. Further, the two individual lines 142, 142' may, as depicted here, be black or exhibit at least one color. Further, the two individual lines 142, 142' may, as depicted here, exhibit the same uniform lateral extension, or their lateral extensions may vary along a length of one or both of the individual lines 142, 142.' Further, the two individual lines 142, 142' may, as depicted here, exhibit a uniform contrast or the contrast may vary along the length of one or both of the individual lines 142, 142.' However, further embodiments may also be feasible.

In the exemplary embodiment as further depicted in FIG. 1, the image 140 which displays the Raubitschek arrow 144 comprises a central point 152, the presentation of which is enhanced by a reticle 154, also denominated as "Bannon's cross," which is, additionally, surrounded by an enclosing circle 156. In this fashion, the determining the at least one astigmatic effect may be assisted, in particular, by facilitating a fixation of the two individual lines 142, 142' by the eye 112 of the person 114 and/or by supporting a rotation 158 of the Raubitschek arrow 144 as described below in more detail.

As already explained above, the eye 112 of the person 114 is capable of recognizing the two individual lines 142, 142' along their entire length without any shadow in a particular case in which the eye 112 of the person 114 is free from at least one astigmatic effect. A view as recognized by the eye 112 of the person 114 in this particular case is illustrated in FIG. 2, ΔD=0.0 D. In this particular case, the investigation of eye 112 of the person 114 can be terminated since a power of the astigmatic effect is zero and an orientation of the axis of the astigmatic effect cannot be defined in this particular case.

However, in further cases, in which the eye 112 of the person 114 can, in fact, recognize a shadow at a portion along one or both of the individual lines 142, 142', the at least one astigmatic effect of the eye 112 of the person 114 can be determined. As described above, determining at least one value for the at least one astigmatic effect of the at least one eye of the person may be performed in accordance with at least one of the following sub-steps:

(i) determining a value for at least one orientation of an axis of the astigmatic effect of the at least one eye 112 of the person 114 from at least two transitions;

(ii) determining a value for at least one power of the astigmatic effect of the at least one eye 112 of the person 114.

Herein, the value for the at least one orientation of the axis of the astigmatic effect according to sub-step (i) may, typically, be determined by performing the rotation 158 of the Raubitschek arrow 144 comprising the two individual lines 142, 142' around the central point 152 in a continuous or step-wise fashion. For this purpose, the image 140 may be rotated on the screen 120, in particular by using a respective algorithm. Alternatively or in addition (not depicted here), the screen 120 may be rotated, in particular by rotating the smartphone 118. Herein, the rotation 158 of the Raubitschek arrow 144 around the central point 152 is performed until the person 114 indicates at a point in time that the two individual lines 142, 142' appear symmetrical with respect to sharpness, darkness, blackness, and/or contrast to the person 114 by using the input unit 122.

For this purpose, the rotation 158 of the continuously or step-wise rotating Raubitschek arrow 144 can actively be stopped by the person 114, specifically by pressing a key of the keypad 130 or the button 132 using a finger 160, or by producing a sound which may be recorded by the microphone 138. Alternatively or in addition, the camera 134 or the motion sensor 136 can be used for determining a gesture movement of the person 114 that may indicate that the two individual lines 142, 142' appear symmetrical with respect to sharpness, darkness, blackness, and/or contrast to the person 114 at the point in time.

Independently of the way the rotation 158 of the image 140 may actually be performed, the value for the orientation of the axis of the astigmatic effect can be determined from an angular value of the rotation 158 of the Raubitschek arrow 144 at the point in time. Herein, the angular value which is determined in this fashion corresponds to the angular value of the orientation of the axis of the astigmatic effect in question. In other words: The desired angular value of the orientation of the axis of the astigmatic effect is parallel to a direction into which the apex 148 of the Raubitschek arrow 144 points.

In a first typical embodiment, the value for the orientation of the axis of the astigmatic effect may be determined prior to the value for the power of the astigmatic effect in accordance with sub-step (ii). However, in an alternatively typical embodiment, the value for the power of the astigmatic effect may be determined according to sub-step (ii) without determining the value for the orientation of the axis of the astigmatic effect before. Herein, the value for the orientation of the axis of the astigmatic effect may be estimated or may be known from a prior measurement of the orientation of the axis of the astigmatic effect. A further alternative is described below with respect to FIG. 3.

In the first embodiment, the Raubitschek arrow 144 which comprises the two individual lines 142, 142' may be displayed for determining the value for the power of the astigmatic effect according to sub-step (ii) in an orientation which corresponds to the value for the orientation of the axis of the astigmatic effect. However, a deviation by an angle of not more than 1°, not more than 2°, not more than 5°, not more than 10°, not more than 20°, or not more than 30°, may also be advantageous as described above.

As illustrated in FIGS. 2 and 3, the individual line 142, 142' which is recognized by the eye 112 of the person 114 having at least one astigmatic effect can be divided along the length of the individual line 142, 142' into at least two different portions, i.e., a first portion 162 in which the individual line 142, 142' exhibits a first appearance to the eye 112 of the person 114 and one or two adjacent second portions 164, 164' in which the individual line 142, 142' exhibits a second appearance to the eye 112 of the person 114, wherein the second appearance of the at least one line 142, 142' to the eye 112 of the person 114 differs from the first appearance of the at least one line 142, 142' to the eye 112 of the person 114. Mainly depending on an individual impression of the person 114, in particular, based on a kind and power of astigmatism and personal experience, the first appearance can, in particular, be described as at least one of a sharp, a dark, a black, or a high contrast appearance of the individual line 142, 142' to the person 114, while the second appearance can, in particular, be described as at least one of a blurred, a bright, a gray, or a low contrast appearance of the individual line 142, 142' to the person 114. As a result of a distribution of the portions 162, 164, 164' along the individual line 142, 142', one or two transitions 166, 166 may occur between the first portion 162 and one or both second portions 164, 164', or vice versa.

As particularly typical, indicating the position of the transition 166, 166' along the individual line 142, 142' can be performed by recording one or more of the following reactions of the person 114 to the image 140 at at least one point in time. Typically, the person 114 can directly indicate the position of the transition 166, 166' on the individual line 142, 142' by touching the position on the touch-sensitive screen 126 using the finger 160. Hereby, a corresponding menu that may be displayed in an information area 168 on the screen 120 of the smartphone 118 can be configured to guide the person 114, accordingly. Alternatively or in addition, the camera 134 or the motion sensor 136 can, typically, be used for determining a gesture movement of the person 114 by observing a behavior of the person 114, in particular a view of the person towards the screen 120 of the smartphone 118 when the individual line 142, 142' is displayed line.

As a further alternative, one or more geometrical figures, such as a horizontal bar 170, may be moved over the touch-sensitive screen 126 by using the finger 160 of the person 114, in particular, until the horizontal bar 170 may rest in a place which may indicate the position of the transition 166, 166.' Alternatively or in addition, the one or more geometrical figures, typically the horizontal bar 170, may be moved over the screen 120 by using a sound as produced by the person 114 and recorded by the microphone 1398 of the smartphone 118. However, a further alternative may also be conceivable.

As a result, the at least one value for the at least one astigmatic effect is, in particular accordance with the present disclosure, determined from the position of the transition 166 on the individual lines 142, 142.' As schematically illustrated in FIG. 2, the value for the power of the astigmatic effect can, typically, be determined from a ratio of a first length of the first portion 162 in which each individual line 142, 142' exhibits the first appearance to the eye 112 of the person 114 versus the second length of the adjacent second portion 164 in which each individual line 142, 142' exhibits the second appearance to the eye 112 of the person 114. In the exemplary embodiment as shown FIG. 2, the horizontal bar 170 can be moved as described above to the corresponding position on the individual lines 142, 142' for determining the transition 166 between the first portion 162 and the second portion 164. As schematically depicted in FIG. 2, the ratio may assume a smaller value as indicated by the horizontal bar 170 for an increasing value of the power $\Delta D$ in D of the astigmatic effect. By way of example, for a power $\Delta D=0.0$ D of the astigmatic effect, the horizontal bar 170 is placed on the bottom 150 of the Raubitschek arrow 144 since no transition 166, 166' occurs here as explained above. By increasing power of the astigmatic effect from $\Delta D=0.6$ D via $\Delta D=1.5$ D, $\Delta D=2.6$ D and $\Delta D=4.1$ D to $\Delta D=6.1$ D, the horizontal bar 170 moves upwards towards the apex 148 of the Raubitschek arrow 144, thus, indicating that the location of the transition 166, 166' on each individual line 142, 142' moves upwards on each individual line 142, 142.' Using a straight-forward algorithm allows determining the value of the power $\Delta D$ in D of the astigmatic effect from the location of the horizontal bar 170 in the image 140.

FIG. 3 illustrates a further exemplary embodiment for determining the value of the power of the astigmatic effect from the transitions 166, 166' between the first portion 162 and two adjacent second portions 164, 164' on a single line 142 from the Raubitschek arrow 144. As depicted there, two individual horizontal bars 170, 170' can, individually, be moved as described above to the corresponding positions on the single line 142 for determining both transitions 166, 166' between the first portion 162 and the adjacent second portions 164, 164.' As indicated there, the value of the power $\Delta D$ in D of the astigmatic effect can be determined for a value of the orientation of the axis of the astigmatic effect of 0° to 90° from the position of the transitions 166, 166' between the first portion 162 and two adjacent second portions 164, 164' on the single line 142 as indicated by the two individual horizontal bars 170, 170' and a midpoint 172 on the line 142. As described below in more detail with respect to FIG. 4, the axis of the astigmatic effect can, typically, be determined by using a position x of the midpoint 172 on the line 142 for a value of the orientation of the axis of the astigmatic effect of 0° to 90°. Only for a value of the orientation of the axis of the astigmatic effect above 90° to below 180°, the second line 142' is further employed.

Without limiting the scope of the disclosure, the evaluation unit 124 as comprised by the smartphone 118 is configured to determine the at least one value for the at least one astigmatic effect of the eye 112 of the person 114, in particular from the ratio of the first length of the first portion 162 versus the second length of the at least one adjacent second portion 164, 164', specifically from the location of the at least one horizontal bar 170, 170' as schematically illustrated in FIGS. 2 and 3. As an alternative or in addition, the evaluation unit 124 may comprise at least one communication interface (not depicted here) which may be configured to exchange data with one or more external servers (not depicted here), which are not comprised by the smartphone 118, wherein the external server is configured to determine the at least one value for the at least one astigmatic effect of the eye 112, typically, in the same fashion.

Figure 4:
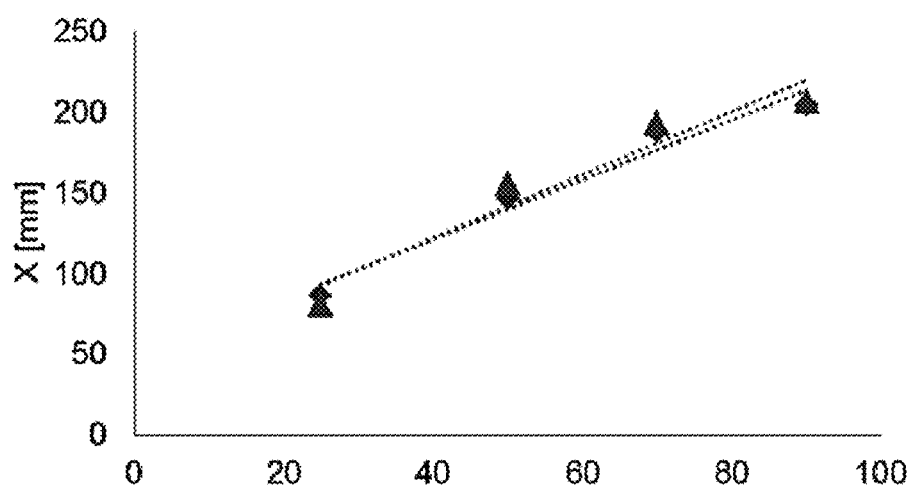
FIG. 4 illustrates an exemplary embodiment of determining an orientation of an axis of the astigmatic effect.

FIG. 4 illustrates an exemplary embodiment of determining a value for the orientation of the axis of the astigmatic effect, e.g. in degrees. As schematically depicted there, a linear function between a difference 4 in the orientation p of a geometrical figure and the orientation a of an actual axis of the astigmatic effect, on one hand, and a position x of the midpoint 172 on the line 142, on the other hand, can be observed by using Equation (1) as follows:

$$\alpha = \Delta + \rho = \frac{x-c}{m} + \rho, \tag{1}$$

wherein m denotes a slope and c a constant offset of the linear function. In particular, the midpoint 172 on the line 142 can be determined as schematically illustrated in FIG. 3. Based on predefined knowledge of m and c and the assessment of the position x of the midpoint 172, the herein described typical embodiment can be used the determine the orientation a of the actual axis of the astigmatic effect.

Figure 5:
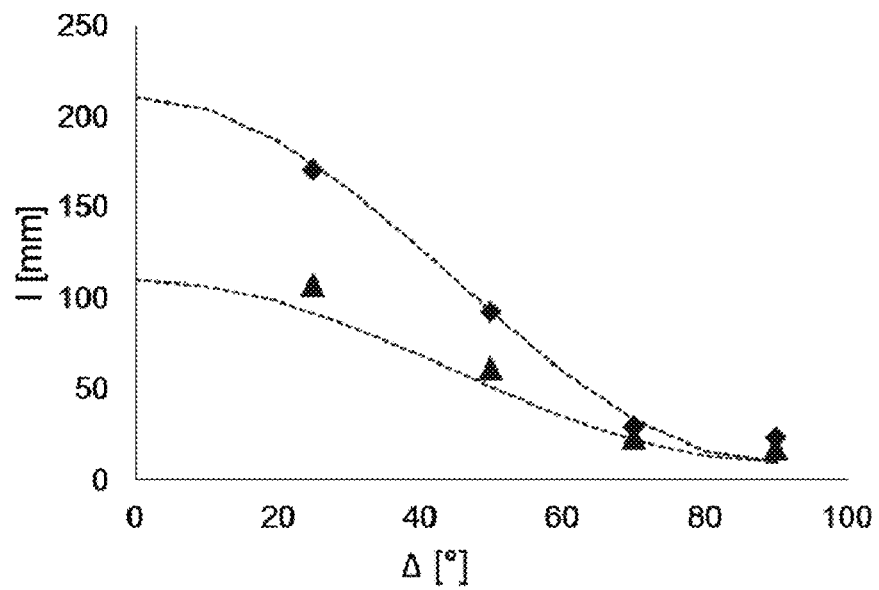
FIG. 5 illustrates an exemplary embodiment of determining the value for the power of the astigmatic effect.

FIG. 5 illustrates an exemplary embodiment of determining the value of the power D of the astigmatic effect, e.g. in diopters. As schematically depicted there, a fitting procedure is applied to length l of the first portion 162 measured as indicated above, such as shown in FIGS. 2 and 3, together with the difference 4 in orientation as determined according to Equation (1) to a $\cos^2$ function, in which an amplitude provides a value for the power D of the astigmatic effect according to Equations (2) and (3) as follows:

$$\ell = \frac{1}{2}\ell_{max} \cdot \frac{1}{D}\cos^2(\Delta) + d \tag{2}$$

$$D = \frac{\cos^2(\Delta) \cdot \ell_{max}}{2(\ell - d)} = D = \frac{\cos^2\left(\frac{x-c}{m}\right) \cdot \ell_{max}}{2(\ell - d)}, \tag{3}$$

wherein d is a constant offset of the $\cos^2$ function and $l_{max}$ denotes the maximum of the line 142 in the image 140 shown to the person 114.

Figure 6:
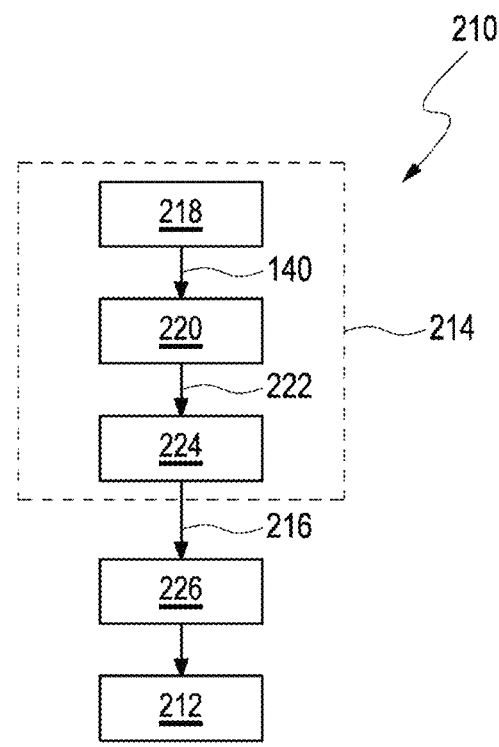
FIG. 6 illustrates an exemplary embodiment of a method for producing a spectacle lens for the at least one eye of the person according to the present disclosure.

FIG. 6 schematically illustrates an exemplary embodiment of a method 210 for producing a spectacle lens 212 for the at least one eye 112 of the person 114.

In a specifying step 214, at least one value 216 for the at least one astigmatic effect of the at least one eye 112 of the person 114 is determined, typically, by using the mobile communication device 116, in particular the smartphone 118.

Herein, the specifying step 214 comprises according to step a), a displaying step 218, during which the at least one image 140, in particular the at least one individual line 142, 142', especially the Raubitschek arrow 144 as exemplarily depicted in FIGS. 1 to 3, is displayed to the eye 112 of the person 114.

Further, the specifying step 214 comprises according to step b), a recording step 220, during which at least one reaction 222 of the person 114 to the at least one image 140 at at least one point in time is recorded, specifically, in a fashion as described above in more detail.

Further, the specifying step 214 comprises according to step c) a determining step 224, during which the desired at least one value 216 for the at least one astigmatic effect of the at least one eye 112 of the person 114 is determined from the reaction 222 of the person 114 to the at least one image 140 at at least one point in time. As described above in more detail, the value for the power of the astigmatic effect is obtained here in accordance with sub-step (ii) but, typically, also the value for the orientation of the axis of the astigmatic effect in accordance with sub-step (i).

For further details concerning the specifying step 214, reference can be made to the description above.

In a processing step 226, the spectacle lens 212 is produced in a fashion which is well-known to the person skilled in the art by processing a lens blank (not depicted here), e.g. by milling or drilling the lens blank, based on instructions which are configured to compensate the at least one value 216 for the at least one astigmatic effect of the at least one eye 112 of the person 114 by using the spectacle lens 212. As a result, a spectacle lens 212, which is produced in this fashion, is capable of compensating the at least one value 216 for the at least one astigmatic effect of the at least one eye 112 of the person 114.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS

110 device (for determining at least one astigmatic effect of at least one eye of a person)

112 eye
114 person
116 mobile communication device
118 smartphone
120 screen
122 input unit
124 evaluation unit
126 touch-sensitive screen
128 input area
130 virtual keypad
132 button
134 camera
136 motion sensor
138 microphone
139 distance
140 image
142, 142' line
144 Raubitschek arrow
146 arrow
148 apex
150 base
152 central point
154 reticle
156 circle
158 rotation
160 finger
162 first portion
164, 164' second portion
166, 166' transition
168 information area
170, 170' horizontal bar
172 midpoint
210 method (for producing a spectacle lens for the at least one eye of the person)
212 spectacle lens
214 specifying step
216 value (for at least one astigmatic effect of at least one eye of a person)
218 displaying step
220 recording step
222 reaction
224 determining step
226 processing step

The invention claimed is:

1. A computer-implemented method for determining at least one astigmatic effect of at least one eye of a person, the method comprising the following steps:
   a) displaying at least one image to at least one eye of a person, wherein the at least one image contains at least one line, wherein the at least one line contains a plurality of sections, and wherein an orientation of each section with respect to an optical axis of the image differs from each other;
   b) recording at least one reaction of the person to the at least one image at at least one point in time with an input unit configured to monitor an occurrence of the at least one reaction by providing or interrupting a monitoring signal at the at least one point in time at which the at least one reaction occurs; and
   c) determining at least one value for at least one astigmatic effect of the at least one eye of the person by evaluating the at least one reaction of the person at the point in time,
      wherein the at least one reaction of the person to the at least one image includes indicating a position on the at least one line, wherein the position on the at least one line refers to at least one transition from a first appearance of the at least one line to the person into a second appearance of the at least one line to the person, or vice versa, wherein the second appearance of the at least one line to the person differs from the first appearance of the at least one line to the person, wherein the at least one transition indicates at least one position on the at least one line in which a first portion in which the at least one line exhibits the first appearance to the eye of the person terminates and at least one adjacent second portion in which the at least one line exhibits the second appearance to the eye of the person commences, or vice versa, wherein the at least one value for the at least one astigmatic effect is determined from the position of the at least one transition on the at least one line, wherein determining the at least one value for the at least one astigmatic effect of the at least one eye of the person includes determining at least one value for at least one power of the astigmatic effect of the at least one eye of the person, and
      wherein the at least one value for the at least one power of the astigmatic effect is determined from a ratio of a length of a first portion of the at least one line exhibiting the first appearance to the person versus the length of at least one adjacent second portion of the at least one line exhibiting the second appearance to the person.

2. The method according to claim 1, wherein step c) further comprises:
   determining at least one value for at least one orientation of an axis of the astigmatic effect of the at least one eye of the person from at least two transitions.

3. The method according to claim 2, wherein the at least one line is displayed for determining the at least one value for the at least one power of the astigmatic effect of the at least one eye of the person with the at least one value for the at least one orientation of the axis of the astigmatic effect as determined, or is estimated or known from a prior measurement thereof.

4. The method according to claim 1, wherein the recording of the at least one reaction of the person to the at least one image at the at least one point in time is implemented through at least one mobile communication device.

5. The method according to claim 4, wherein the at least one mobile communication device comprises at least one screen which displays a visual leveling cue including a guideline to assist the person in maintaining a constant level relationship between the at least one mobile communication device and the person while the at least one reaction of the person is recorded.

6. The method according to claim 1, wherein indicating the position of the at least one transition on the at least one line from the first appearance to the person into the second appearance to the person, or vice versa, according to step b), comprises at least one of:
   pointing at the position of the at least one transition on the at least one line on at least one touch-sensitive screen of at least one mobile communication device by using at least one finger of the person;
   determining at least one gesture movement of the person by using at least one of a camera or a motion sensor of the at least one mobile communication device;
   moving at least one geometrical figure over the at least one touch-sensitive screen of the at least one mobile communication device by using the at least one finger of the person;

moving the at least one geometrical figure over the at least one screen of the at least one mobile communication device by using a voice of the person.

7. The method according to claim 1, wherein step a) comprises displaying two individual lines.

8. The method according to claim 7, wherein the rotation of the two individual lines is performed by at least one angular value around a central point of the two individual lines until the two individual lines are, according to step b), indicated by the person at the point in time as symmetrical with respect to at least one of sharpness, darkness, blackness, or contrast to the person, wherein the at least one value for the at least one orientation of the axis of the astigmatic effect is determined from the at least one angular value of the rotation of the two individual lines with respect to at the point in time.

9. The method according to claim 7, wherein the two individual lines produce an arrow having an apex and a base, wherein the two individual lines become parallel to each other at the apex of the arrow, and wherein the two individual lines point in opposite directions at the base of the arrow, wherein the two individual lines touch each other at the apex of the arrow.

10. A computer program stored on a non-transitory storage medium and comprising instructions which, when the program is executed by a computer, cause the computer to carry out a method for determining at least one astigmatic effect of at least one eye of a person, the method comprising the following steps:
 a) displaying at least one image to at least one eye of a person, wherein the at least one image contains at least one line, wherein the at least one line contains a plurality of sections, wherein an orientation of each section with respect to an optical axis of the image differs from each other;
 b) recording at least one reaction of the person to the at least one image at at least one point in time with an input unit configured to monitor an occurrence of the at least one reaction by providing or interrupting a monitoring signal at the at least one point in time at which the at least one reaction occurs; and
 c) determining at least one value for at least one astigmatic effect of the at least one eye of the person by evaluating the at least one reaction of the person at the point in time,
  wherein the at least one reaction of the person to the at least one image includes indicating a position on the at least one line, wherein the position on the at least one line refers to at least one transition from a first appearance of the at least one line to the person into a second appearance of the at least one line to the person, or vice versa, wherein the second appearance of the at least one line to the person differs from the first appearance of the at least one line to the person, wherein the at least one transition indicates at least one position on the at least one line in which a first portion in which the at least one line exhibits the first appearance to the eye of the person terminates and at least one adjacent second portion in which the at least one line exhibits the second appearance to the eye of the person commences, or vice versa, wherein the at least one value for the at least one astigmatic effect is determined from the position of the at least one transition on the at least one line, wherein determining the at least one value for the at least one astigmatic effect of the at least one eye of the person includes determining at least one value for at least one power of the astigmatic effect of the at least one eye of the person, and
  wherein the at least one value for the at least one power of the astigmatic effect is determined from a ratio of a length of a first portion of the at least one line exhibiting the first appearance to the person versus the length of at least one adjacent second portion of the at least one line exhibiting the second appearance to the person.

11. A method for producing at least one spectacle lens for at least one eye of a person, wherein the producing of the at least one spectacle lens includes processing at least one lens blank by adjusting at least one optical parameter of the at least one spectacle lens, wherein the processing of the lens blank is based on instructions configured to compensate at least one astigmatic effect of the at least one eye of the person, wherein the determining of the at least one astigmatic effect of the at least one eye of the person comprises the following steps:
 a) displaying at least one image to at least one eye of a person, wherein the at least one image contains at least one line, wherein the at least one line contains a plurality of sections, and wherein an orientation of each section with respect to an optical axis of the image differs from each other;
 b) recording at least one reaction of the person to the at least one image at at least one point in time with an input unit configured to monitor an occurrence of the at least one reaction by providing or interrupting a monitoring signal at the at least one point in time at which the at least one reaction occurs; and
 c) determining at least one value for at least one astigmatic effect of the at least one eye of the person by evaluating the at least one reaction of the person at the point in time,
  wherein the at least one reaction of the person to the at least one image includes indicating a position on the at least one line, wherein the position on the at least one line refers to at least one transition from a first appearance of the at least one line to the person into a second appearance of the at least one line to the person, or vice versa, wherein the second appearance of the at least one line to the person differs from the first appearance of the at least one line to the person, wherein the at least one transition indicates at least one position on the at least one line in which a first portion in which the at least one line exhibits the first appearance to the eye of the person terminates and at least one adjacent second portion in which the at least one line exhibits the second appearance to the eye of the person commences, or vice versa, wherein the at least one value for the at least one astigmatic effect is determined from the position of the at least one transition on the at least one line, wherein determining the at least one value for the at least one astigmatic effect of the at least one eye of the person includes determining at least one value for at least one power of the astigmatic effect of the at least one eye of the person, and
  wherein the at least one value for the at least one power of the astigmatic effect is determined from a ratio of a length of a first portion of the at least one line exhibiting the first appearance to the person versus the length of at least one adjacent second portion of the at least one line exhibiting the second appearance to the person.

12. A device for determining at least one astigmatic effect of at least one eye of a person, the device comprising:
- at least one screen, wherein the at least one screen is configured to display at least one image to at least one eye of a person, wherein the at least one image contains at least one line, wherein the at least one line contains a plurality of sections, and wherein an orientation of each section with respect to an optical axis of the image differs from each other;
- at least one input unit, wherein the input unit is configured to record at least one reaction of the person to the at least one image at at least one point in time by providing or interrupting a monitoring signal at the at least one point in time at which the at least one reaction occurs; and
- at least one evaluation unit, wherein the at least one evaluation unit is configured to determine at least one value for at least one astigmatic effect of at least one eye of the person by evaluating the at least one reaction of the person at the point in time, or wherein the at least one evaluation unit comprises at least one communication interface configured to exchange data with at least one server, wherein the at least one server is configured to determine at least one value for at least one astigmatic effect of at least one eye of the person by evaluating the at least one reaction of the person at the point in time,
- wherein the at least one input unit is configured to record the at least one reaction of the person to the at least one image indicating a position on the at least one line, wherein the position on the at least one line refers to at least one transition from a first appearance of the at least one line to the person into a second appearance of the at least one line to the person, or vice versa, wherein the second appearance of the at least one line to the person differs from the first appearance of the at least one line to the person, wherein the at least one transition indicates at least one position on the at least one line in which a first portion in which the at least one line exhibits the first appearance to the eye of the person terminates and at least one adjacent second portion in which the at least one line exhibits the second appearance to the eye of the person commences, or vice versa, wherein the at least one value for the at least one astigmatic effect is determined from the position of the at least one transition on the at least one line, wherein determining the at least one value for the at least one astigmatic effect of the at least one eye of the person includes determining at least one value for at least one power of the astigmatic effect of the at least one eye of the person, and
- wherein the at least one value for the at least one power of the astigmatic effect is determined from a ratio of a length of a first portion of the at least one line exhibiting the first appearance to the person versus the length of at least one adjacent second portion of the at least one line exhibiting the second appearance to the person.

13. The device according to claim 12,
- wherein the at least one screen is further configured to display a rotation of two individual lines by at least one angular value, or wherein at least one gyro sensor configured to determine at least one orientation of the two individual lines in space and, therefrom the rotation of the two individual lines by the at least one angular value,
- wherein the at least one input unit is configured to record the at least one reaction of the person at the at least one point in time when the two individual lines appears symmetrical with respect to at least one of sharpness, darkness, blackness, or contrast to the person, and
- wherein the at least one evaluation unit is further configured to determine at least one value for at least one orientation of an axis of the astigmatic effect from the angular value of the rotation of the two individual lines at the at least one point in time.

14. The device according to claim 12, further comprising
- at least one of a camera or a motion sensor configured to determine at least one gesture movement of the person;
- at least one touch-sensitive screen configured to determine a position of the at least one transition on the at least one line by recoding a touching of at least one finger of the person;
- at least one microphone configured to determine a position of the at least one transition on the at least one line by recoding a voice of the person; and
- a distance meter, wherein the distance meter is configured to determine at least one distance.

* * * * *

UNITED STATES PATENT AND TRADEMARK OFFICE
CERTIFICATE OF CORRECTION

Page 1 of 1

PATENT NO. : 12,042,224 B2
APPLICATION NO. : 18/165448
DATED : July 23, 2024
INVENTOR(S) : Alexander Leube et al.

It is certified that error appears in the above-identified patent and that said Letters Patent is hereby corrected as shown below:

In the Specification

In Column 27, Line 33: change "difference 4 in the orientation p" to -- difference $\Delta$ in the orientation $\rho$ --

In Column 27, Line 34: change "orientation a" to -- orientation $\alpha$ --

In Column 27, Line 50: change "orientation a" to -- orientation $\alpha$ --

In Column 27, Line 56: change "difference 4" to -- difference $\Delta$ --

In Column 28, Line 1: change "$l_{max}$" to -- $\ell_{max}$ --

Signed and Sealed this
Twenty-fifth Day of February, 2025

Coke Morgan Stewart
*Acting Director of the United States Patent and Trademark Office*